(12) United States Patent
Eggers et al.

(10) Patent No.: US 6,461,624 B2
(45) Date of Patent: **\*Oct. 8, 2002**

(54) SKIN-PROTECTIVE COMPOSITION

(76) Inventors: Sabine Eggers, 11 Manor Downs, Thornbury View, Rochestown, County Cork (IE); James Clair, 1 Woodlands, Cloghroe, Blarney, County Cork (IE); Michael John Van Der Meer, Marian House, Ballydulae, County Cork (IE)

(\*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,095
(22) PCT Filed: Jun. 18, 1998
(86) PCT No.: PCT/IE98/00048
§ 371 (c)(1), (2), (4) Date: Dec. 17, 1999
(87) PCT Pub. No.: WO98/58627
PCT Pub. Date: Dec. 30, 1998

(65) Prior Publication Data
US 2002/0048592 A1 Apr. 25, 2002

(30) Foreign Application Priority Data
Jun. 20, 1997 (IE) .............................. S970463
Oct. 2, 1997 (IE) ................................. 970713

(51) Int. Cl.[7] .............................................. A61K 7/00
(52) U.S. Cl. ....................................................... 424/401
(58) Field of Search ......................................... 424/401

(56) References Cited

U.S. PATENT DOCUMENTS

| | | | | |
|---|---|---|---|---|
| 2,900,306 A | | 8/1959 | Slater ........................... | 167/90 |
| 4,268,498 A | \* | 5/1981 | Gedeon et al. ................ | 424/59 |
| 5,126,136 A | | 6/1992 | Merat et al. ................... | 424/49 |
| 5,208,013 A | \* | 5/1993 | Klein ........................... | 424/59 |

FOREIGN PATENT DOCUMENTS

| | | |
|---|---|---|
| DE | 3339196 A1 | 8/1985 |
| DE | 19602111 A | 7/1997 |
| EP | 0702950 A | 3/1996 |
| EP | 0709091 A | 5/1996 |

(List continued on next page.)

OTHER PUBLICATIONS

Kosaku, Yasunishi, Chemical Abstracts, vol. 94, No. 14, Apr. 1981, p. 404.

(List continued on next page.)

Primary Examiner—Jose' G. Dees
Assistant Examiner—Konata M. George
(74) Attorney, Agent, or Firm—Birch, Stewart, Kolasch & Birch, LLP

(57) ABSTRACT

The present invention relates to a protective composition for skin, which protects against bacterial, viral and fungal infections. The compositions comprise a $C_8$–$C_{20}$ fatty acid, one or more parabens or a combination of these. The compositions of the invention are particularly effective in controlling infections by Methicillin Resistant *Staphylococcus aureus* (MRSA) as well as other organisms. The invention includes protective hand creams such as barrier hand creams, as well as body lotions, liquid soaps, shampoos, soap bars and creams generally, which are all protective.

12 Claims, 8 Drawing Sheets

FOREIGN PATENT DOCUMENTS

| | | | |
|---|---|---|---|
| EP | 0709092 | A | 5/1996 |
| EP | 0770379 | A | 5/1997 |
| EP | 0803192 | A | 10/1997 |
| FR | 1337769 | A | 12/1963 |
| FR | 2293924 | A | 7/1976 |
| GB | 675152 | | 7/1952 |
| WO | 9209260 | A | 6/1992 |
| WO | 9316690 | A | 9/1993 |
| WO | 9415461 | | 7/1994 |
| WO | 9526710 | | 10/1995 |
| WO | 9611572 | A | 4/1996 |
| WO | 9811887 | A | 3/1998 |
| WO | 9816104 | A | 4/1998 |
| WO | 9820872 | A | 5/1998 |

OTHER PUBLICATIONS

Raza Aly et al., Applied and Environmental Microbiology, Jun. 1976, p. 931–935.

Raza Aly et al., Applied and Environmental Microbiology, Mar. 1979, pp. 610–613.

R.L. Boddie et al., Journal of Dairy Science, vol. 75, No. 6, 1992, pp. 1725–1730.

D.A. Dance et al., Journal of Hospital Infection, vol. 10, 1987, pp. 6–10.

J.J. Kabara, Nutrition Reviews, vol. 38, No. 2, 1980, pp. 65–73.

J. J. Kabara, Antimicrobials in Foods, 1983, pp. 109–129.

F.A. Kapral et al., Journal of Medical Microbial, vol. 37, 1992, pp. 235–237.

B. B. Knudsen et al., Contact Dermatitis, vol. 24, 1991, pp. 45–49.

N. J. Reynolds et al., Contact Dermatitis, vol. 22, 1990, pp. 103–104.

J. Ojajärvi, Hands as Vectors of Disease, 1978, pp. 1–16.

* cited by examiner

SKIN-PROTECTIVE COMPOSITION

The present invention relates to a protective composition for skin which protects against bacterial, viral and fungal infection In particular, the invention relates to anti-infective (infection preventing) products, to be used to control infections caused by gram positive organisms such as Methicillin Resistant *Staphylococcus aureus* (MRSA), Pneumococci and Vancomycin Resistant Enterococci (VRE) as well as gram negative bacteria such as *Escherichia coli* and *Pseudomonas aeruginosa*. The invention provides a durable handcream which is retained on the hands despite use of the hands. More particularly the invention relates to a protective handcream of the type known as a "barrier" handcream. The invention also provides body lotions, liquid soaps, shampoos, soap bars and creams generally, which are protective.

BACKGROUND OF THE INVENTION

Although medical science is continually advancing with new techniques and drugs being developed almost daily, cross-infection in hospitals is still a common occurrence with major implications. Micro-organisms may be acquired and transmitted by one of the following routes: direct contact, airborne or via fomites. Although these routes are well understood and procedures to control them are standard practice, pathogenic organisms still exist in the hospital environment.

The spread of infection by direct contact is considered to be the most important method of transmission both for gram positive and gram negative organisms, and it is agreed that the hands of hospital personnel play an important role in the transmission of infection.

Many different organisms exist on the skin. Some belong to the normal flora of the skin and are harmless commensals, which may however, on occasion, become opportunist pathogens in patients who are unusually susceptible to infection such as those in intensive care units. Organisms on the skin can be classified into three categories:
Transient organisms—micro-organisms which are deposited on the skin but do not multiply there;
Temporary residents—contaminants which multiply on the skin and persist for short periods;
Resident organisms—permanent inhabitants of the skin which colonise the deeper crevices of the skin and hair follicles.

Removal or killing of the transient flora is generally considered sufficient to prevent the transfer of cross-infection in hospital, but removal of the resident flora is an additional advantage which should be achieved if possible.

Skin disturbances lead to difficulties in the process of skin cleansing Patients with eczema are often colonised by *Staphylococcus aureus* to a greater extent than even those suffering from the strongly scaling disease psoriasis. Patients with an atopic eczema are also more frequently colonised because their skin is not as smooth as those with completely healthy skin. Extensive and frequent use of antiseptic-detergent preparations, such as those used in hospitals, causes moderate to severe drying of the skin of the hands, and indeed small wounds on the fingertips in some cases. Low relative humidity during winter results in additional stress to the skin. More than half the nurses involved in one clinical study had increased numbers of bacteria on their hands after only one week's use of an antiseptic detergent preparation (Ojajarvi, J. 1978). The increase was thought to be due to the drying and skin damaging effects of frequent hand washing between every patient contact, but the age of the personnel and nature of duties undertaken were also contributory factors.

Currently a source of major concern is the appearance of resistant strains of bacteria which survive the cleansing processes, and which have become resistant to antiseptics, antibacterials and antibiotics which originally destroyed them. No amount of hand washing is capable of removing these micro-organisms. Of particular importance amongst the gram positives are resistant strains of *Staphylococcus aureus* (Methicillin Resistant *Staph. aureus*—MRSA), resistant Pneumococci and Enterococci (Vancomycin Resistant Enterococci—VRE).

There is an ever increasing awareness of the need to reduce cross infections in hospitals This awareness has increased with the appearance of these resistant strains The spread of these infections now has enormous consequences for patient care with patients during, hospital stay increasing, and hospital budgets soaring. Drugs used to fight MRSA are now responsible for up to 10% of the drug bill at some U.S. hospitals.

Guidelines prepared by Health Departments around the world recommend, in the absence of anything better, that hand washing is the most important factor currently available in preventing the spread of MRSA and other pathogenic bacteria. These guidelines recommend washing the hands with an antiseptic detergent (e.g. Chlorhexidine-containing hand washes), before and after each patient contact.

The research of Ojajarvi (1978) referred to above shows the limitations of these recommendations. Furthermore, the work of Aly and Maibach (1979) proved that chlorhexidine significantly reduced the normal flora of the hands. These synthetic antiseptic containing preparations suppress the protective gram positive population (Aly & Maibach, 1976), resulting in a potentially harmful shift towards gram negative colonisation. Long-term and frequent use of detergents containing synthetic bacteriostatic agents may lead to detrimental overgrowth of a particular bacterial species which would otherwise have been unable to survive on normal healthy skin.

In addition, allergic contact dermatitis caused by chlorhexidine gluconate and diacetate has been reported by Reynolds et al. (1990) and Knudsen et al.(1991). By far the most alarming problem was the incidence of a hospital outbreak of Chlorhexidine-resistant *Proteus mirabilis* resulting in an outbreak of urinary-tract infections affecting 90 patients in Southampton between July 1980 and May 1985 (Dance et al. 1987).

These results show that handwashing alone can not prevent the spread of infections.

Boddie et al 1992, J. Dairy Sci. 75 1725–1730 discusses the use of post-milking teat germicides containing Lauricidin (Registered Trade Mark for glycerol monolaurate), saturated fatty acids, lactic acids and lauric acid. Various compositions were determined against new IMI (intra-mammary infection) caused by *Staphylococcus aureus* and *Streptococcus agalactiae* in three controlled infection trials.

Each of the compositions contained Lauricidin (TM) and lactic acid. Two of the compositions further contained lauric acid.

Kabara (1983) "Medium Chain Fatty Acids and Esters" discusses the history of various types of soaps, and further discusses the suitability of various fatty acids as food additives. It is stated therein that it is well established that unsaturated fatty acids exhibit an antibacterial influence on gram-positive micro-organisms. The inhibitory effects of unsaturated fatty acids are stated to increase as the number of double bonds in the molecule increase.

International Application PCT/US95/02588 (Publication No. WO 95/26710) discusses a personal skin moisturising and cleansing bar composition which comprises both a skin cleansing agent and a lipid moisturising agent in the same bar, which deposits an effective amount of the lipid on the skin of the user in a bath or shower. The bar composition contained both Na lauric soap and lauric acid. The bar thus cleanses and leaves a moisturising lipid layer on the skin. It is not said to have any anti-microbial properties and does not take the form of a leave-on cream or lotion.

U.K. Patent Application No. 675,152 discloses oleaginous cosmetic cleansing creams which are used to loosen and dissolve dirt from the skin and which are easily removed from the skin using water alone. Use in these compositions of monoesters of substantially saturated fatty acids of about 12 to 18 carbon atoms with saturated aliphatic polyhydric alcohols of 2 to 3 carbon atoms is disclosed. The composition of Examples 2 to 7 discloses the use of a para hydroxy benzoic acid as a preservative. It is expressly stated that this preservative proved not to be needed in the formulations of these Examples. The creams are distinct from those of the present invention in that they are designed to be removed from the skin and do not have anti-microbial properties.

German Patent Application No. DE 3 339 196 discloses laurylamido-ethyl-trimethylammonium chloride and its use as an antimicrobial preservative and disinfectant.

U.S. Pat. No 2,900,306 relates to a deodorant stick, comprising a solid alcohol base and having dispersed therein a water soluble soap or salt of saturated higher fatty acids having essentially 12 to 14 carbon atoms. This product is a deodorant not an to anti-microbial cream.

OBJECT OF THE INVENTION

The object of the invention is to produce a product which overcomes all of the above mentioned problems. In particular the object of the present invention therefore is to produce a topical preparation which would be:

supplemental to handwashing—(or in place of where necessary); antibacterial—(against gram positive, especially MRSA and VRE, and gram negative bacteria such as *E.coli*);

antifungal and antiviral, of natural origin as far as possible—(thereby reducing the chance of resistance occurring), hypoallergenic—(thereby reducing the possibility of contact dermatitis);

acting as a protective "chemical" glove—(thereby always maintaining sterility);

inexpensive—(so as to be affordable to all hospital budgets);

attractive to use—(so that hospital staff will not want to avoid hand sterilization as is currently often the case).

Further objects of the invention are:

(a) To use a naturally occurring compound as active ingredient, which might reduce the incidence of resistance and allergies.

(b) To provide a product that nourishes the skin and thereby prevents drying and skin damage due to frequent use of antibacterial detergents.

(c) To replace natural components of the skin that are vital parts of the antibacterial defence system of the skin that are removed by washing.

(d) To create an active "liquid glove" (protective mantle) on the skin that prevents infections by the above mentioned bacterial species.

(e) To provide an attractive, reasonably inexpensive agent that is easy to use and does not require handwashing facilities.

SUMMARY OF THE INVENTION

According to the present invention there is provided a protective composition for inhibiting bacterial growth on the skin comprising (i) a physiologically acceptable carrier or base;
(ii) a preservative,
(iii) an active ingredient for protecting the skin; and
(iv) a skin protectant characterised in that the active ingredient is selected from a $C_8$ to $C_{20}$ fatty acid, one or more parabens, or a combination thereof.

The fatty acid is preferably lauric acid or a lauric acid salt such as a sodium salt. The fatty acid is present in an amount of 0.05 to 5% w/v, preferably 0.2 to 1% w/v and more preferably 0.5% w/v.

A paraben or a combination of parabens may be present in the composition. Suitable parabens are methyl and propyl paraben or a combination of methyl and propyl paraben. The composition can suitably contain methyl and propyl parabens in about a 1-1 ratio (w/v). Methyl and propyl paraben are preferably present in an amount of 0.05 to 1% w/v, preferably 0.2 to 0.3% w/v and more preferably 0.25% w/v.

A suitable skin protectant is Simethicone (also known as Dimethicone) Simethicone can be present in an amount of 3 to 10% w/v, preferably 4 to 6% w/v and more preferably 5% w/v.

As an optional extra ingredient, the protective composition may contain an antioxidant, such as Vitamin E (alpha-tocopherol) in an amount of 0.2 to 1% w/v, preferably 0.4 to 0.6% w/v and more preferably 0 5% w/v The invention also provides the use of a $C_8$ to $C_{20}$ fatty acid as defined above for use in the manufacture of a protective composition for inhibiting the growth of bacteria, particularly Methicillin Resistant *Staphylococcus aureus* (MRSA), Vancomycin Resistant Enterococci and gram negative organisms, particularly coliforms and pseudomonants. One or more parabens may also be used to prepare the protective composition.

The invention also provides the use of $C_8$ to $C_{20}$ fatty acid in the inhibition of bacterial, fungal and viral growth and more particularly the use of such a fatty acid together with one or more parabens to inhibit bacterial, fungal or viral growth.

Suitably the paraben can act both as an active ingredient and as a preservative in the above defined composition. The fatty acids are active against both gram positive and gram negative organisms while parabens are particularly active against gram negative organisms.

DETAILED DESCRIPTION

In order to achieve the objectives mentioned above it was decided to use products already found in the body and which have been shown to have natural antimicrobial activity. Being naturally occurring they should be hypoallergenic at active concentrations. Certain constituents of milk have been shown to have anti-viral and antibacterial activity (see discussion of Boddie et al, 1992, J. Dairy Sci. 75:1725–1730 above). The active factor appears to be a fatty acid $C_{18:2}$. Fatty acids and their antimicrobial activity have also been described. Both fatty acids and monoglycerides have these properties and are well documented in the literature. Lactic acid, another naturally occurring component is also known to be inhibitory to both Gram-positive and Gram-negative organisms. A cream in accordance with the invention comprises:

(a) fatty acids ($C_8$–$C_{20}$) and their salts preferably lauric acid ($C_{12}$) sodium salt in concentrations of 0.05–5.0%, preferably 0.2 to 1%, more preferably 0.5% w/v.

It is believed that certain derivatives of lauric acid e.g. Lauricidin (glycerol monolaurate) exhibits anti-infective properties in the treatment Intra-Mammary Infections (IMI) as reported by Boddie el al. 1992. Moreover, monoesters of lauric acid are thought to prevent transmission of viruses such as AIDS, hepatitis B and herpes and are therefore used in a liquid antiseptic handwash (GB-B-2193892 of Colgate Palmolive Company) The antiviral activity of milk isolated in the fatty acid fraction has been reported (Kabara, J. J. 1980)

Esters of fatty acids were not incorporated into the product since it is well known that the Fatty Acid Modifying Enzyme (FAME) inactivates a series of bactericidal fatty acids ($C_{11}$–$C_{24}$) by esterifying them with certain alcohols as reported by Kapral et al 1992.

(b) A skin protectant. Simethicone (also known as Dimethicone), a mixture of dimethyl polysiloxanes and silica gel, acts as a skin protectant and is used in many established "skin protecting" formulations to ensure the retention of the active ingredients on the skin. Here used in a concentration of 3–10%, preferably 4 to 6%, more preferably 5% w/v.

(c) A well-established cream base (oil in water) preserved by a potent antimicrobial preservative system such as Parabens or Nipa Esters™ (available from Nipa Laboratories Ltd., U.K.) (e.g. methyl and propyl paraben sodium salts) with supporting anti-infective properties. The preferred concentration of a 1:1 mixture of parabens is 0.05–1% w/v, preferably 0.2 to 0 3% w/v, more preferably 0.25% w/v.

Parabens are known to be effective in low concentrations against both bacteria and fungi Propylparaben is considered to be antifungal (Merck index)

The cream may also optionally contain.

Vitamin E (alpha-tocopherol) acts as a antioxidant. It is used in concentrations of 0.2–1% preferably 0.4 to 0.6%, more preferably 0.5% w/v. It prevents oxidation of essential cellular constituents and prevents the formation of toxic oxidation products formed from unsaturated fatty acids that have been detected in its absence.

Structures of

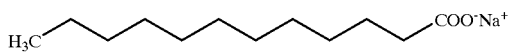

methyl paraben sodium salt (II) and propyl paraben sodium salt (III)

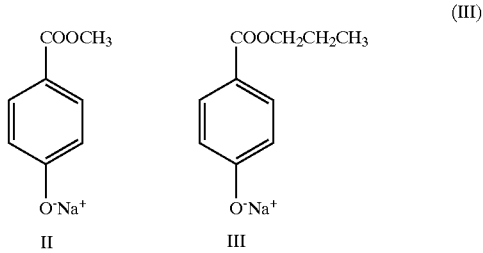

After washing with an antiseptic detergent or antiseptic soap, if necessary, the barrier cream of the invention is applied by rubbing a fixed, dispensed amount into the hands. The application of further amounts of cream can be done at any stage. The cream has the advantage over normal antiseptic soaps that the active ingredient, once applied, act continuously on the skin and is not washed off, after application, as is the case with the antiseptic soaps. Dispensers for the cream can be placed wherever convenient, and a source of water for washing is not essential. The application of this formulation is not limited to hospitals or consulting rooms but may be used by anyone dealing with the public at large and in danger of infection such as bank tellers, bus conductors, etc. Other possible users are those involved in the production of pharmaceuticals and food products. It is not the intention to replace hand washing altogether but rather to use the cream to maintain sterility after handwashing or in places where hand washing is not possible.

It is also intended that the cream could be used as an antiseptic wound dressing for wounds which are or may become infected by bacteria.

It is also intended that the barrier cream can be applied as a total body application for those patients who are too fragile to move or bath and who might be colonised by bacteria, viruses or fungi, resistant or otherwise.

In a series of tests the moisturising cream base has been found to be highly acceptable to both male and female users indicating that the product will probably be used more often than the use of hand washing with antiseptic soaps.

In a manner similar to that for creams described above, soaps, liquid soaps, body lotions, shampoos or the like, can be made in accordance with the invention.

METHODS

Well Diffusion Assay

Figure 1A:
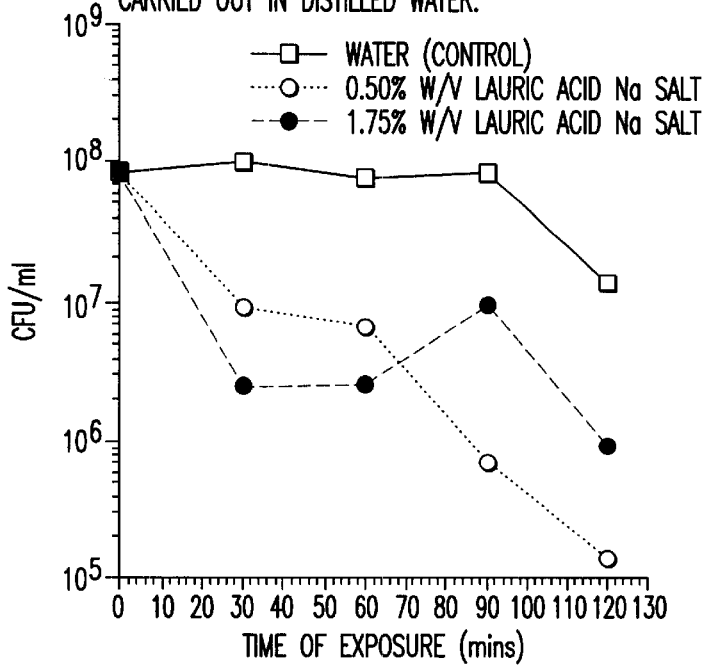
FIGS. 1a+b: Viable counts of MRSA strain S13 in the presence of varying concentrations of Lauric acid Na salt. The MRSA strain S13 was chosen in all assays since it is the most resistant isolate to the parabens.

An overnight culture of the bacterium in question was diluted 1 1,000 in sterile ¼×Ringers solution and 1 ml of this was used to inoculate 500 mls of sterile Tryptic Soy Agar (TSA). Note TSA is a complex medium which is capable of sustaining a wide variety of bacteria. 20 ml aliquots of this seeded agar were then poured into sterile petri-dishes and allowed to solidify.

After solidification the desired number of wells were sucked out of the agar using an inverted pasteur pipette which was attached to a vacuum manifold.

One of these wells was designated the control well for all tests and to this 50 μl of the solvent used to dilute the test compounds was added.

When the test reagents were added all plates were incubated at the optimum temperature for the bacterium concerned, 30° C. for Pseudomonas aeruginosa and 37° C. for all other bacteria, the right way up.

Determination of the Cell Counts

This was achieved by a number of different techniques depending on the circumstances involved. The techniques used were:

1. Standard spread plate technique

This involves spreading a 100 μl aliquot of the desired dilution onto well dried agar plates using an alcohol flamed hockey stick.

2. Pour plate technique

In this method 1 ml samples of the diluted culture are placed into a sterile petri dish and then sterile cooled agar is added. The plate is then gently swirled to facilitate a heterogeneous mixing of the sample and the agar and allowed to solidify before being incubated at the temperature of choice in an inverted manner.

3. Spot/drop plating method

This method involves the placing of a sample or the diluted sample onto a pre-dried agar plate but the sample is allowed to dry into the plate. Usually an aliquot of 5–20 μl is chosen to be thus plated. This method offers the advantages of being both economical in terms of agar plates (several drops can be readily accommodated on one agar plate) and also accurate.

All plates were incubated for 16 hours before being counted.

All dilutions were carried out in ¼×Ringers solution and all bacteria were grown up in Tryptic Soy Broth (TSB)

Determination of the cell survival/percentage killing of a culture with respect to exposure to a given agent.

In this method a sample of a fresh overnight culture was titred and a sample (usually 5 mls) was added to either broth (100mls) containing the test reagents or sterile water (100 mls) and test agents.

Immediately a sample ($T_0$) was taken and plated using one of the techniques listed above. At regular intervals thereafter other samples were also removed, diluted and plated.

These results were then counted and graphed. Error is 1 standard deviation of the mean.

Definitions Used bactericidal the suffix cide (Latin: cida, to kill), refers to any agent (chemical or physical) which is able to kill (at least) some types of (vegetative) bacteria, some agents can also irreversibly inactive bacterial spores bacteriostatic the suffix static (Greek: staticos causing to stand or stopping), refers to any agent which inhibits the growth and (particularly) the reproduction of (at least) some types of (vegetative) bacteria.

killing the resultant inability of individual cells to grow when plated onto agar and incubated at their optimum temperature having been exposed to anti-infective agent. sources of citations Singleton, Sainsbury, Dictionary of Microbiology, Wiley & Sons.

| Reagents | State | Solvent | Stock conc |
|---|---|---|---|
| lauric acid | powder | distilled water | 0.25–5% w/v |
| lauric acid sodium salt | desiccated | distilled water | 0.25–5% w/v |
| methylparaben sodium salt | powder | distilled water | 0.1–5% w/v |
| propyl paraben sodium salt | powder | distilled water | 0.1–5% w/v |

Results

The Effect of Lauric Acid Sodium Salt on MRSA

The cell killing effects of lauric acid sodium salt on MRSA was studied and the results shown in FIGS. 1a and b.

As can be seen the effects of lauric acid Na salt are quite profound in respect to isolate S 13, 0.50% lauric acid Na salt is capable of reducing a population of MRSA in water held at 37° C. by 99.8% over 2 hrs. However, this seems to be an anomaly in that the higher concentration of the lauric acid Na salt (1.75%) was not as efficient in its killing effect <99.0% killing over the same period of time. This would seem to imply that the availability of water would play an essential role on the killing effect experienced by MRSA.

Figure 1B:
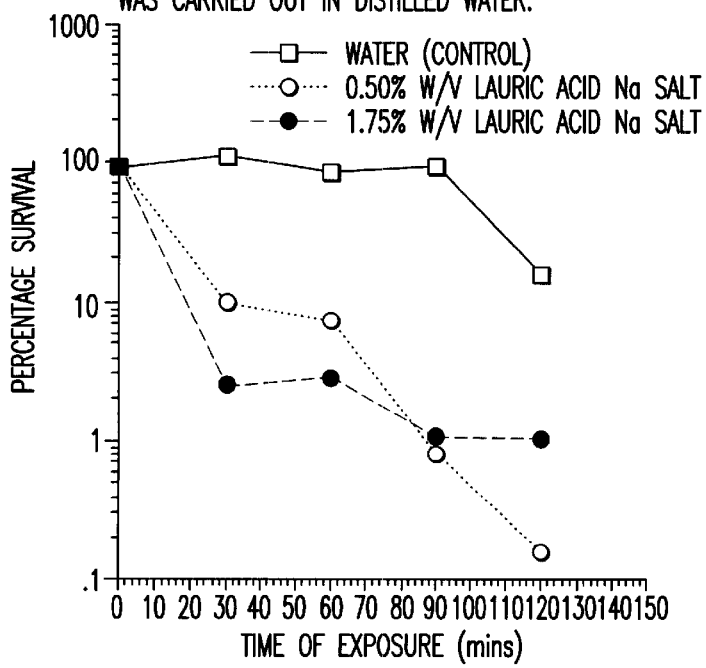
Figure 2A:
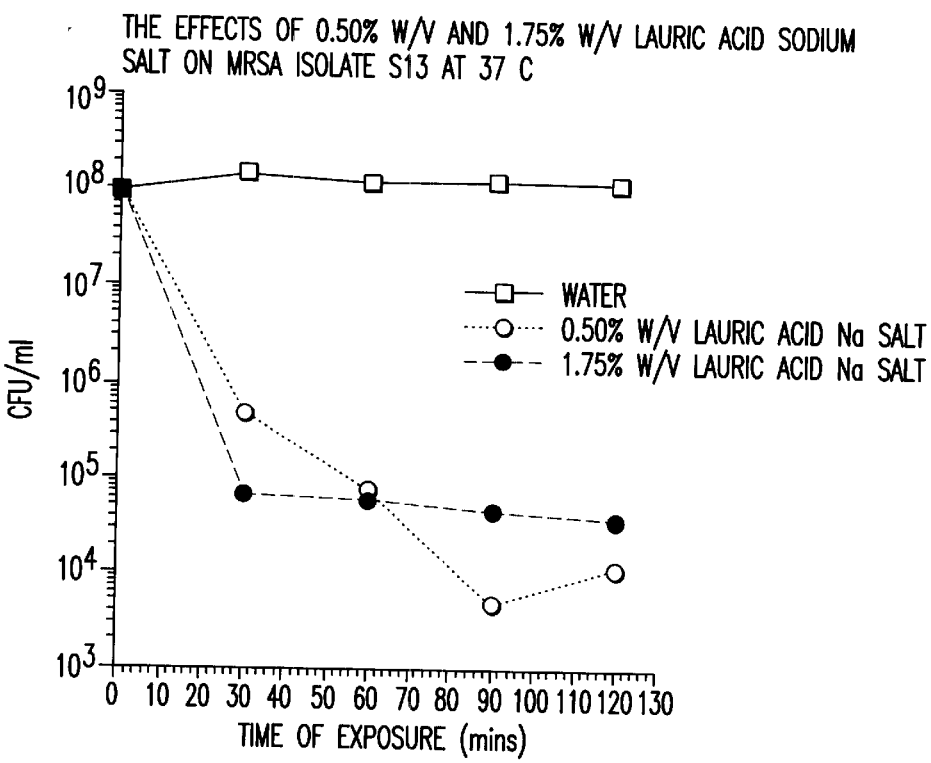
FIGS. 2a+b: The effects of 0.50% and 1.75% (w/v) solutions of lauric acid Na salt on MRSA isolate S13 at 37° C.

This experiment was then repeated and the results shown in FIGS. 2a and b. From FIG. 1b it can be seen that 1.75% (w/v) of lauric acid Na salt acts more rapidly than 0.50% but its effects would appear to level off rapidly as if there was only a subpopulation that was sensitive to this concentration, while its killing effect is closely followed by the 0.50% lauric acid Na salt which again is capable of killing a greater number of MRSA 99.6% killing after 30 mins.

Figure 2B:
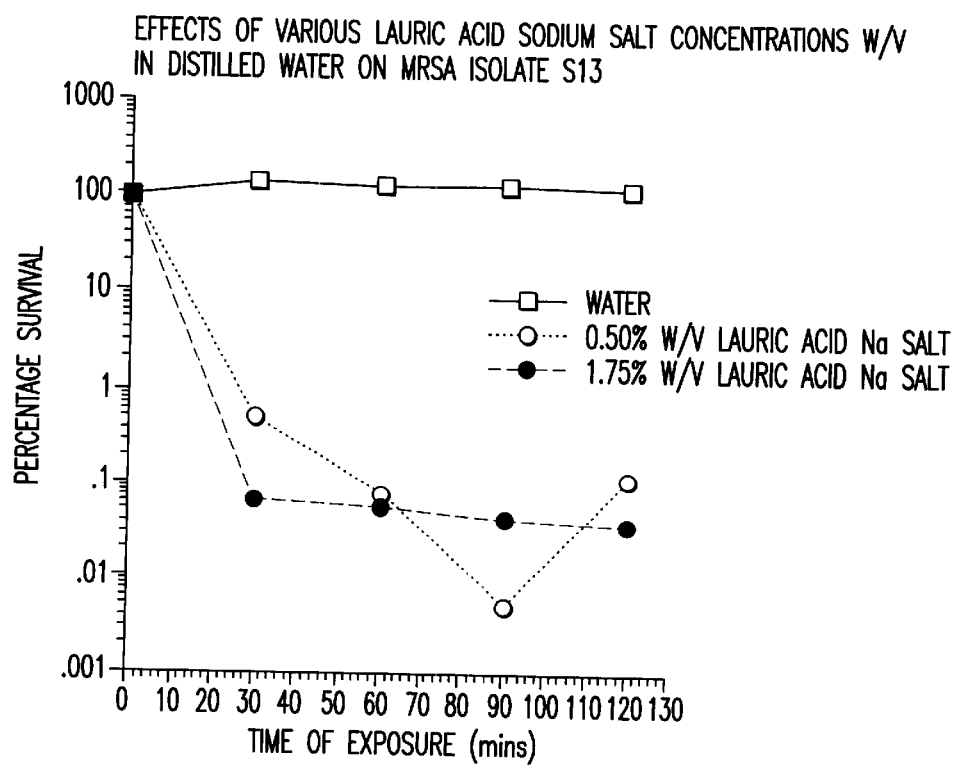

The results shown in FIGS. 1 and 2 differ because of evaporation of the alcohol carrier necessary to keep the higher concentration of lauric acid in solution. Once evaporated the activity would stop as no more lauric acid would be available having precipitated out.

Role of Methyl and Propyl Paraben

Figure 3:
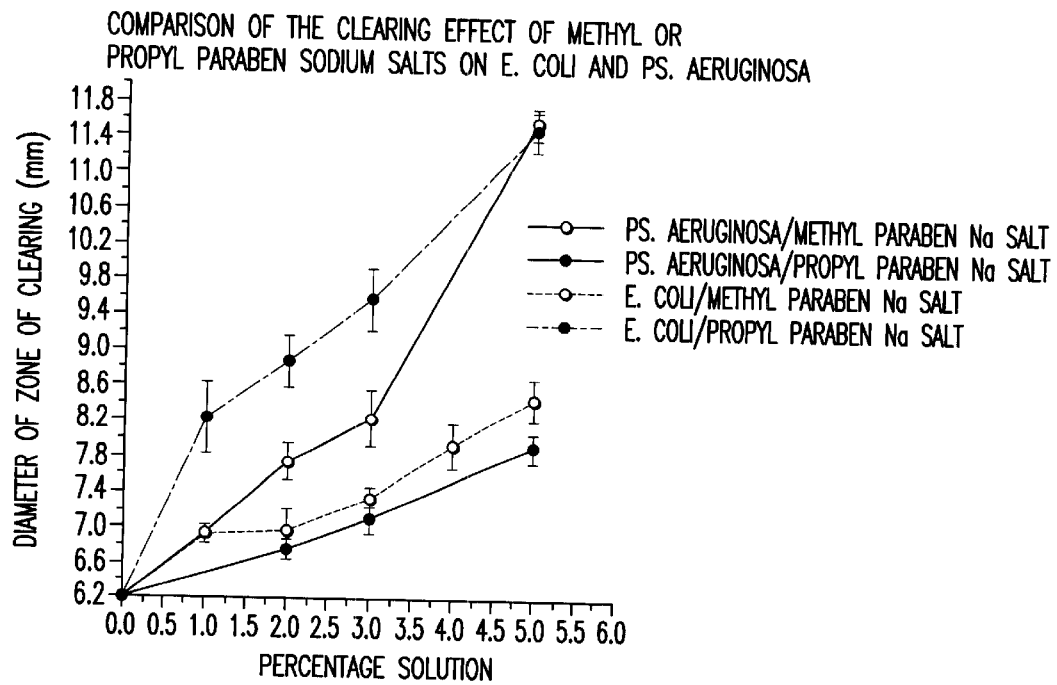
FIG. 3 Comparison of the clearing effect of individual methyl or propyl paraben Na salts on E coli and Ps. aeruginosa.
Figure 4:
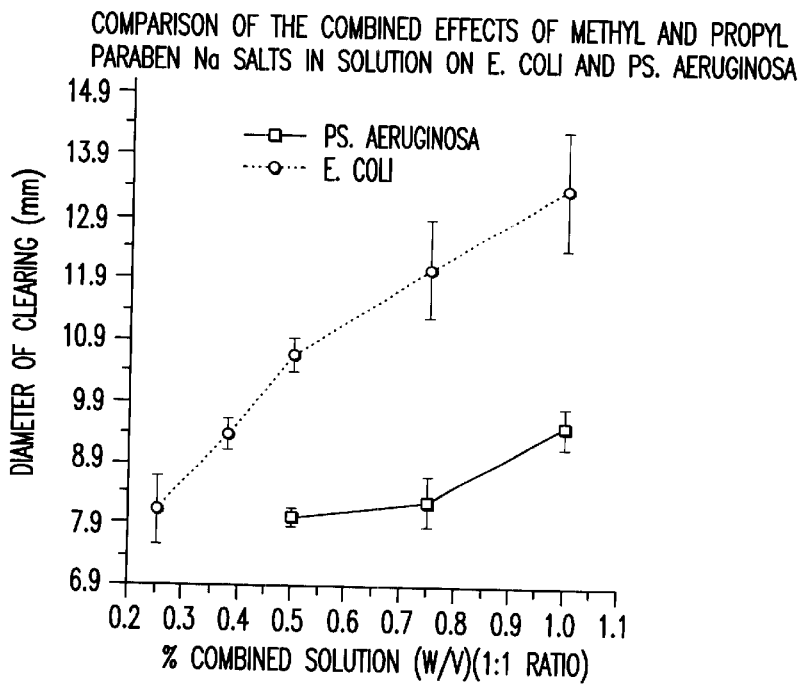
FIG. 4 Comparison of the combined effects of methyl and propyl paraben Na salts (in solution) on E. coli and Ps. aeruginosa.

The effects of both methyl and propyl paraben Na salts on gram-negatives were studied when added individually and the results given in FIG. 3. This was assayed using the well diffusion technique. Note that there is a difference in the sensitivity of E.coli and Ps. aeruginosa to the different paraben derivatives. Notice also that their concentrations are 1–5% (w/v), The effects of both methyl and propyl paraben Na salts combined in a 1:1 ratio on gram-negatives are shown in FIG. 4. Notice that the concentration required to give a significant clearing zone has been reduced extraordinarily presumably due to synergistic effect obtained by the combination of the two parabens.

Figure 5A:
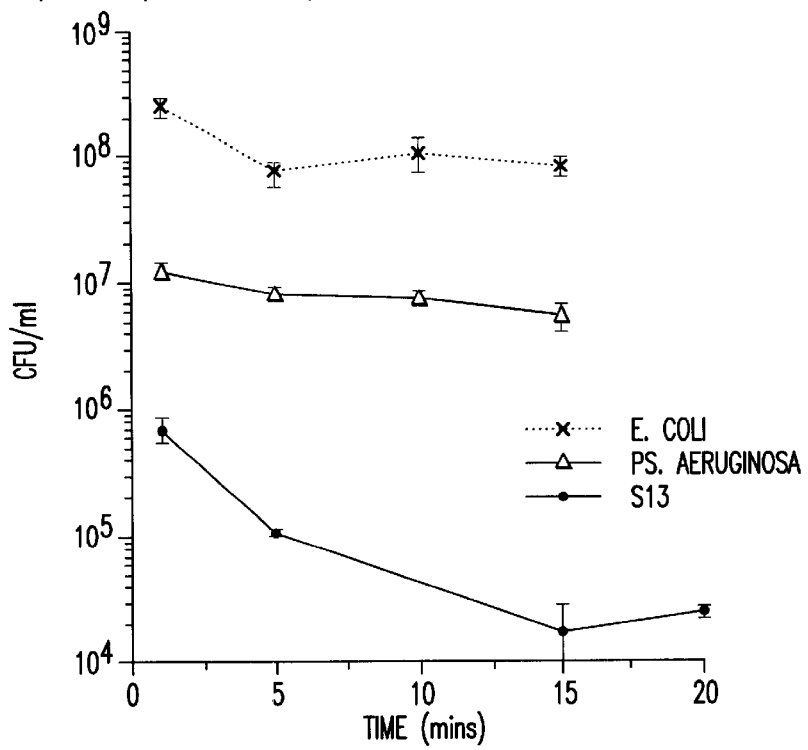
FIGS. 5a+b: Effects of 0.25% (w/v) methy/propyl paraben Na salt (1:1 ratio) and 0.50% (w/v) of lauric acid Na salt on selected bacterial stains.
Figure 5B:
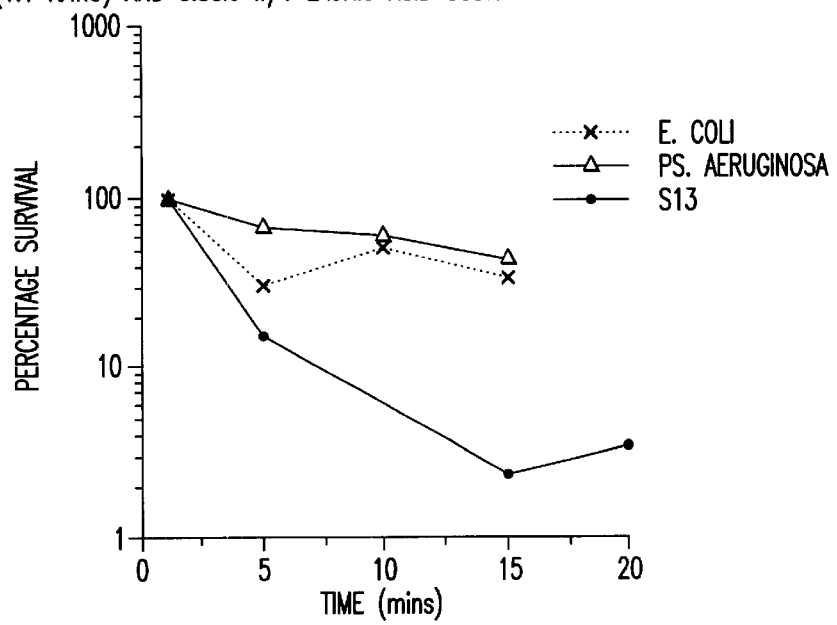

From FIGS. 5a+b it was determined that the mode of action of the parabens was primarily bactericidal in respect to the gram negatives and the MRSA S13 isolate.

Figure 6A:
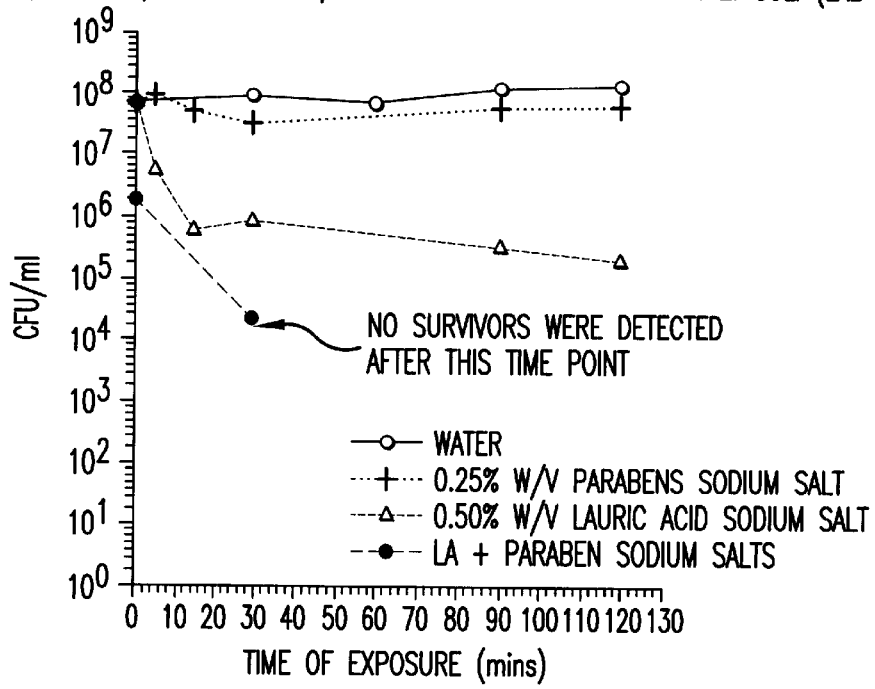
FIGS. 6a+B: Effects of methyl/propyl paraben Na salt 0.25% (w/v) (1:1 ratio) and/or lauric acid Na salt 0.50% (w/v) on E. coli (lab isolate)+survival of E. coli in the presence of methyl/propyl paraben Na salt 0.25% (wv) (1:1 ratio) and/or lauric acid Na salt 0.50% (w/v).
Figure 6B:
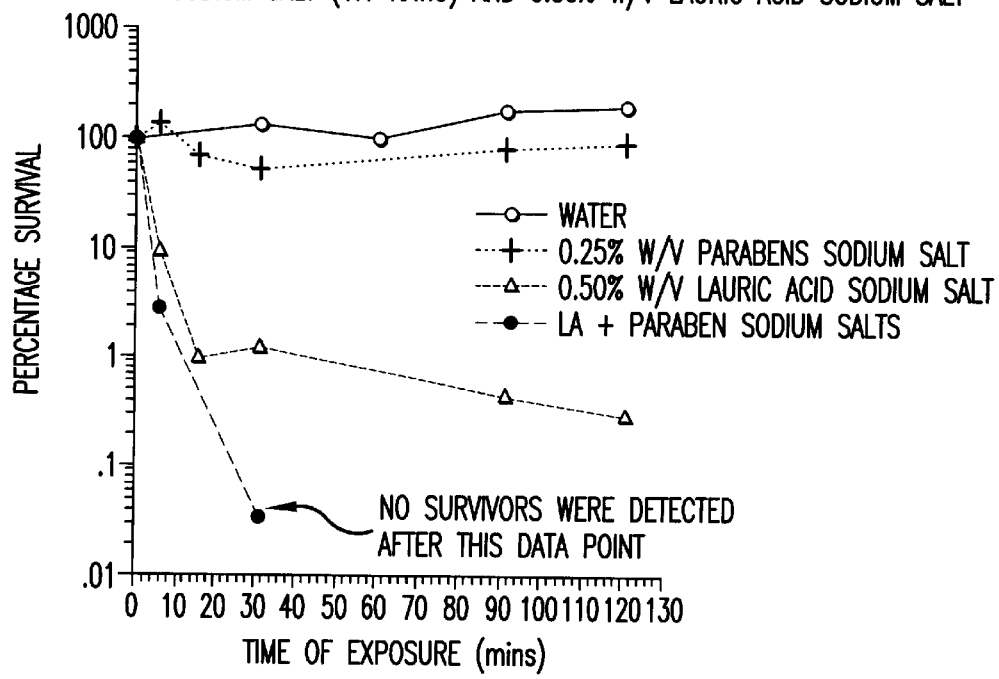

The results shown in FIGS. 6a and b indicate that lauric acid Na salt in combination with the parabens acts as a bactericidal since the starting number of organisms $10^8$ dropped 2 logs within 30 sec. No survivors were detected after 35 mins. This action is presumably due to a synergistic effect since none of the isolated components is capable of killing E. coli that efficiently.

Figure 7A:
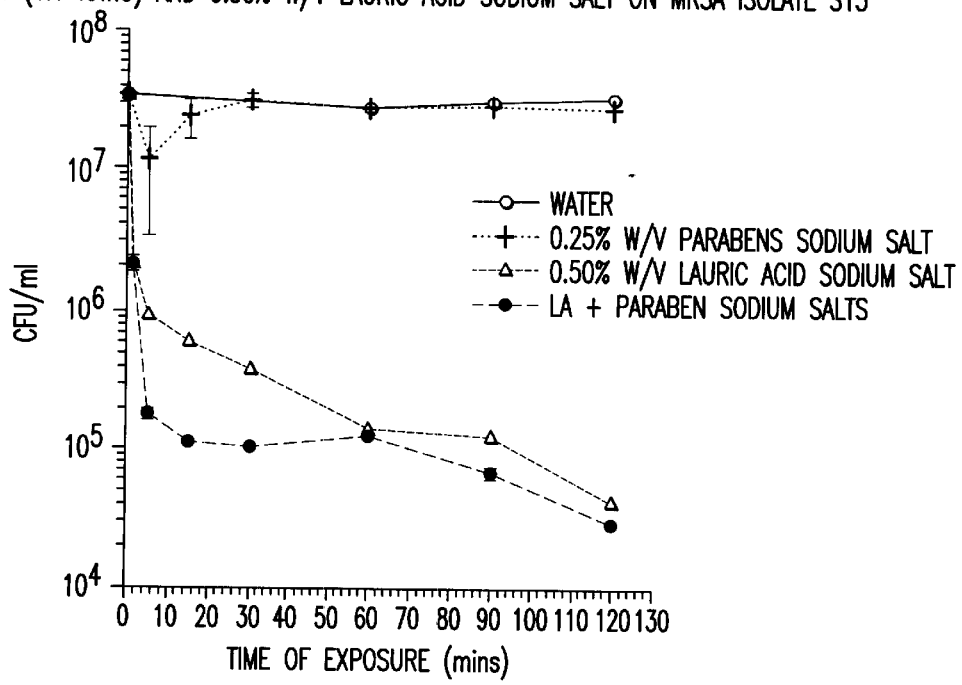
FIGS. 7a+b: Effects of methyl/propyl paraben Na salt 0.25% (w/v) (1:1ratio) and/or lauric acid Na salt 0.50% (w/v) on MRSA isolate S13+survival of MRSA isolate S13 in the presence of methyl/propyl paraben Na salt 0.25% (w/v) (1:1 ratio) and/or lauric acid Na salt 0.50% (w/v).
Figure 7B:
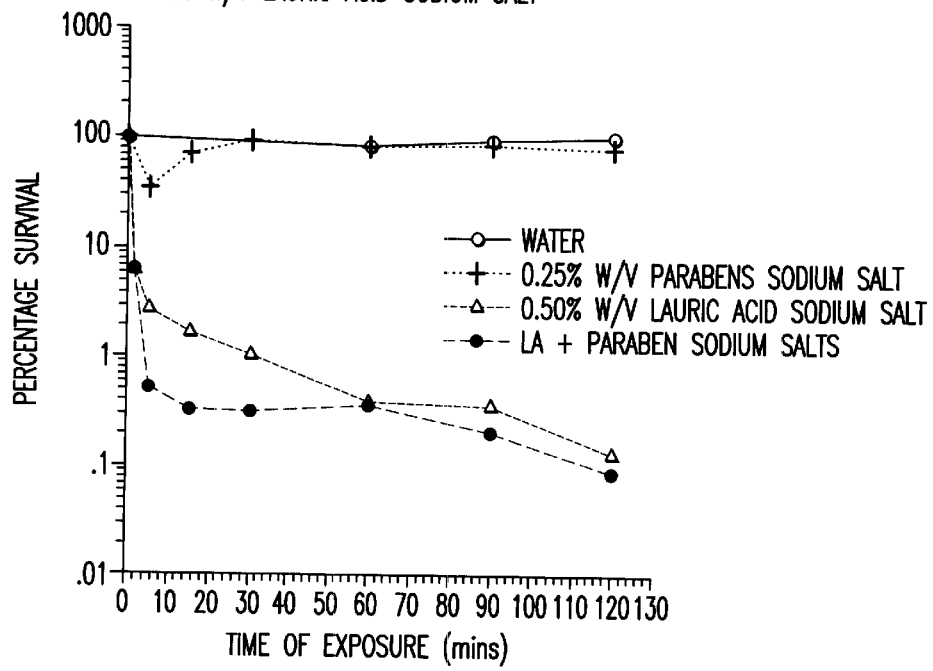

As shown in FIGS. 7a and b the parabens have little or no effect on the MRSA isolate. This would have been expected as this strain was chosen for its resistance to the paraben mixture. Lauric acid does elicit killing effect, but again the combination of the parabens and the lauric acid Na salt seems to act synergistically and most efficiently.

Figure 8A:
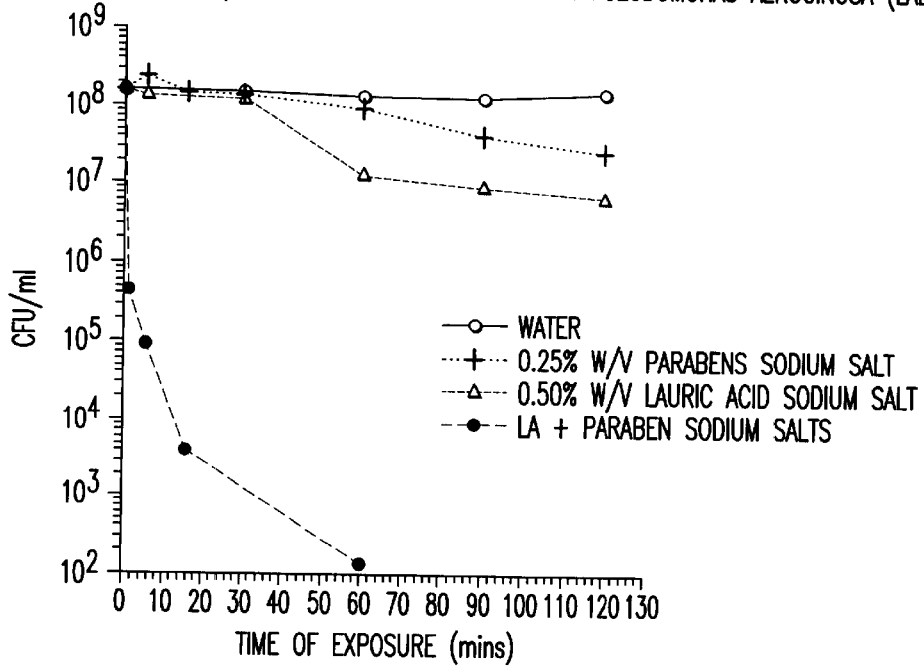
FIGS. 8a+b: Effects of methyl/propyl paraben Na salt 0.25% (w/v)(1:1 ratio) and/or lauric acid Na salt 0.50% (w/v) on+Ps. aeruginosa (lab isolate) +survival of Ps. aeruginosa (lab isolate) in the presence of methyl/propyl paraben Na salt 0.25% (w/v).
Figure 8B:
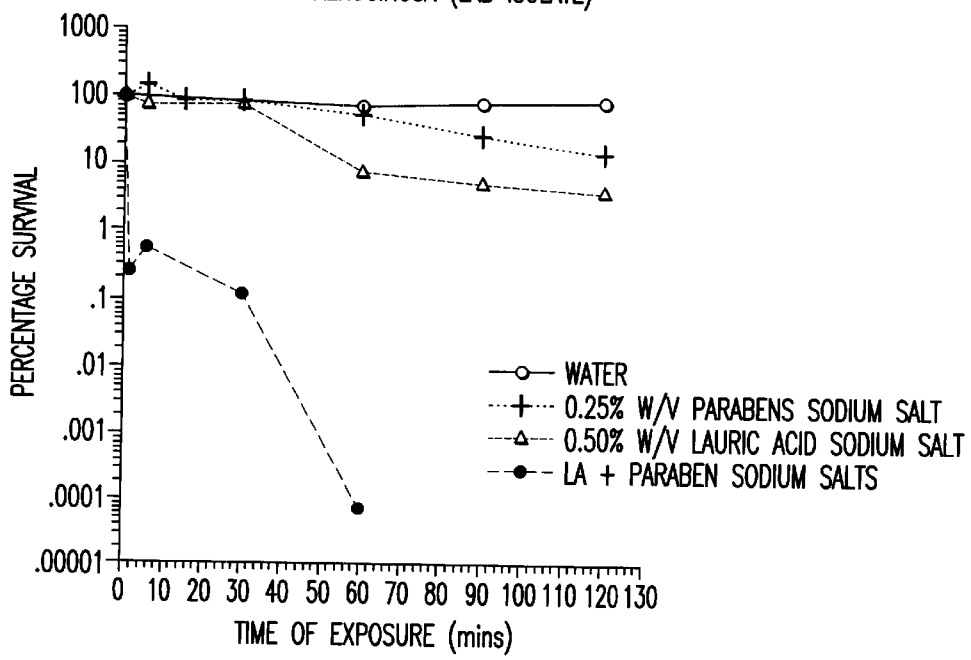
Figure 9A:
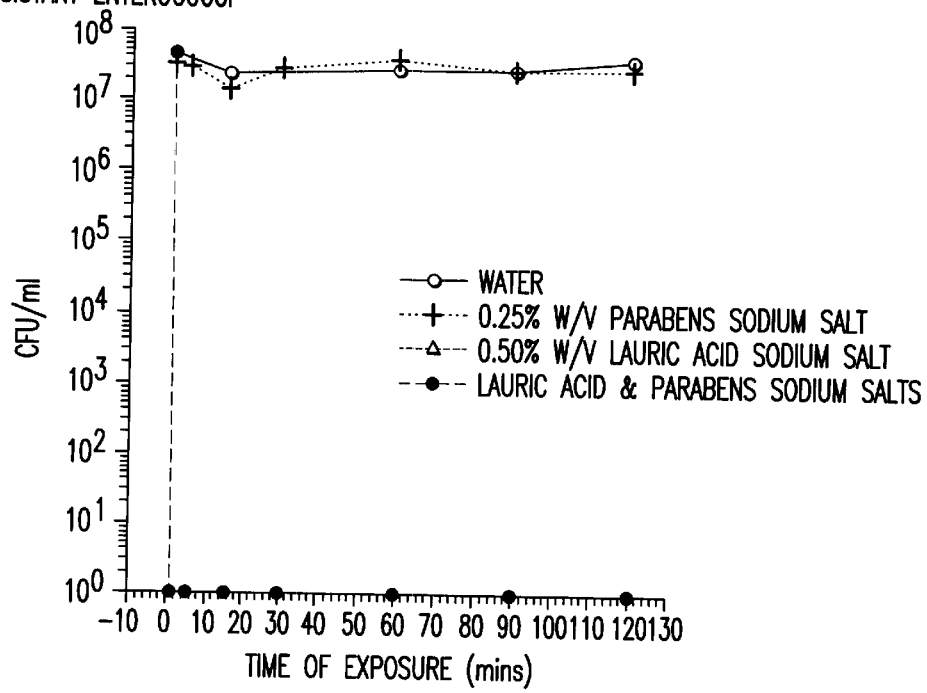
FIGS. 9a+b: Effects of methyl/propyl paraben Na salt 0.25% (w/v) (1:1 ratio) and/or lauric acid Na salt 0.50% (w/v) on Vancomycin-resistant enterococci+survival of Vancomycin-resistant Enterococci in the present of methyl/propyl paraben Na salt 0.25% (w/v) (1:1 ratio) and/or lauric acid Na salt 0.50% (w/v).
Figure 9B:
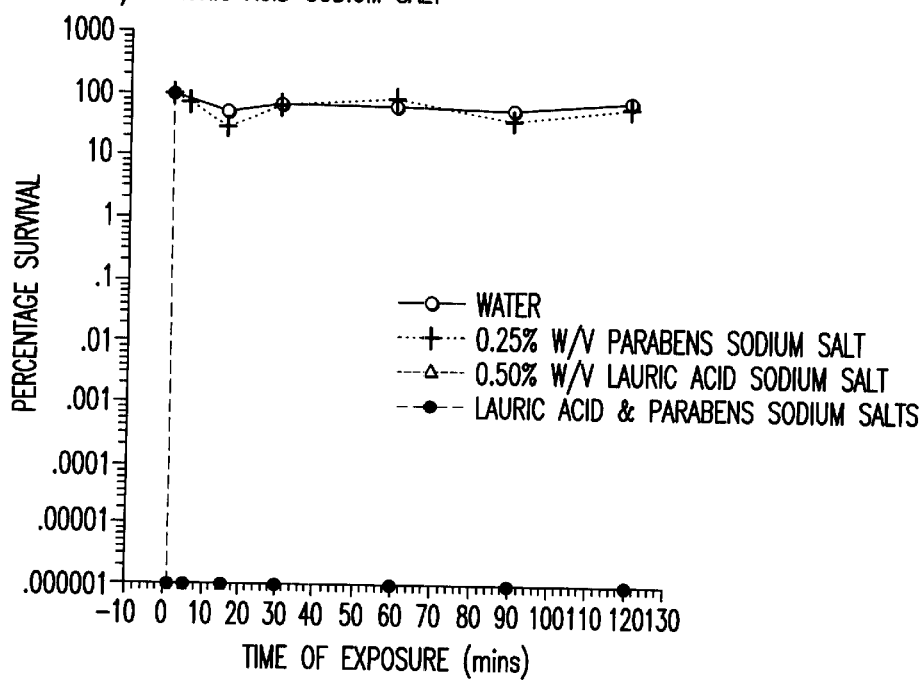

FIGS. 8a and b show that lauric acid Na salt is not effective against gram-negative Ps. aeruginosa although some killing does occur. There is slight killing due to the parabens but the combination of lauric acid Na salt and the parabens proves once again to result in a synergistic effect. Anti-Bacterial Efficacy of Lauric Acid Na Salt in Comparison to the Parabens The results shown in FIGS. 9a and b demonstrate that the parabens have no effect against enterococci in comparison to lauric acid Na salt and the combination of lauric acid Na salt and the parabens. Lauric acid Na salt alone or in combination with the parabens is bactericidal and kills off Vancomycin-resistant Enterococci instantaneously since no survivors were found to be present when the samples were plated after 5 mins The control sample which was incubated at the same temperature was able to remain at the same levels as when initially inoculated: $4.63 \times 10^7$ cfu/ml (cfu=colony forming units) was the $T_0$ count. This indicates that a 100% kill rate was experienced.

Use of 0.50% of Lauric Acid Na Salt

These results give strong evidence to endorse the use of 0.50% lauric acid Na salt as opposed to a higher concentration as an even higher rate of killing is achieved using the lower dose. It may however take slightly longer to achieve using 0.50% of lauric acid Na salt but this killing time is relatively rapid and therefore the lower level could be used rather than>1% of lauric acid Na salt.

In Vivo Studies

A survey in December 1990 of potential users among medical staff showed the *Staphylococcus aureus* hand carriage rate to be 19.1% (MRSA 5.35%). This was at a time when a previously known handwash was used routinely as a hand disinfectant. A blind clinical trial was carried out on 21 volunteers using the cream of the invention after handwashing with ordinary, non-antiseptic soap and compared them with 26 who abstained from washing their hands with the previously known handwash but who used ordinary, non-antiseptic soap only for three days. None of the individuals applying the barrier cream had evidence of *S. aureus* on their hands. In contrast, five of the 26 (19.2%) volunteers using non-antiseptic soap only had *S. aureus* on their hands.

A follow up survey showed the hand carriage rate of *S. aureus* among medical staff to be 3% (1% MRSA). We have found no *S. aureus* carriages on the hands of staff who routinely used the barrier cream. All these in vivo studies were performed single-blind, i e the users were unaware of the composition or expected effects of the cream The components of the cream are highly efficient in inhibiting gram-positive and gram-negative organisms such as:

Methicillin-resistant *Staphylococcus aureus*(MRSA)
Pneumococci
Enterococci (especially Vancomyan-resistant Enterocci)
*Escherichia coli*
*Pseudomonas aeruginosa*

The barrier cream has great potential for reducing cross-infection by hand contact with the above mentioned organisms. There is no evidence of any unwanted effects (e.g., skin irritation) on hands after prolonged usage.

Tests carried out indicate excellent staff compliance as the cream is popular due to its non-greasy natural feel and as the condition of skin on the hands is improved.

Example of Barrier Cream—Formulation

| Cream Composition | | % w/v of the total composition g |
|---|---|---|
| Cream base | emulsifying wax (Lanette Sx) | 9.0 |
| | white petroleum jelly | 15.0 |
| | liquid paraffin | 6.0 |
| active ingredient | lauric acid sodium salt | 0.5 |
| preservative | methyl paraben and propyl paraben sodium salts (1.1) | 0.25 |
| antioxidant | alpha-tocopherol | 0.5 |
| barrier | dimethicon 350 | 5.0 |
| fragrance | camalia | 0.35 |
| | dem. water | 63.40 |

Methyl paraben is sold under the Trade Mark NIPAGIN M. PROPYL paraben is sold under the Trade Mark NIPASOL (available from Nipa Laboratories Ltd., Glamorgan, U.K.)

Summary of Results of in Vitro Research

Percentage of cells killed after 5 minutes exposure to various active ingredients:

| Bacterium | 0.5% lauric acid Na salt | 0.25% Parabens Na sat | lauric acid Na salt + Parabens Na salt |
|---|---|---|---|
| E. coli | >90 | 0 | >99 |
| Ps. aeruginosa | >13 | 0 | >99 |
| MRSA (S13) | >97 | >65 | >99 |
| Vancomycin Resistant Enterococcus | 100 | 33 | 100 |

All bacteria tested were sensitive to the effects of lauric acid to a greater or lesser extent Vancomycin-resistant Enterococci were totally destroyed by lauric acid alone *Pseudomonas aeruginosa* showed only 13% destruction with lauric acid alone, no effect with the Parabens only but almost total destruction with the combination. This demonstrates a synergistic effect between lauric acid and the Parabens against Pseudomonas. The effect on MRA (S 13) was also increased by the inclusion of the Parabens, however lauric acid alone was responsible for more than 97% destruction after 5 minutes. The effects of lauric acid Na salt on the Vancomycin-resistant Enterococcus (FPL050) were also tested. This strain appears to be extremely sensitive to lauric acid as no survivors were found to be present when samples were plated after 5 mins.

REFERENCES

Aly, R. and Maibach, H. I. (1976), Effect of antimicrobial soap containing chlorhexidine on the microbial flora of skin, Appl. Environ. Microbiol. 31, 931–5.

Aly, R. and Maibach, H. I. (1979), Comparative study on the antimicrobial effect of 0.5% chlorhexidine gluconate and 70% isopropyl alcohol on the normal flora on hands, Appl. Environ. Microbiol. 37 855–7.

Boddie, R. L. and Nickerson, S. C. (1992), Evaluation of post-milking teat germicides containing Lauricidin, saturated fatty acids, and lactic acid, J. Dairy Sci. 75, 1725–30.

Dance, D. A., Pearson., A. D. Seal, D. V., and Lowes, J. A. (1987), A hospital outbreak caused by a chlorhexidine and antibiotic-resistant+Proteus mirabilis, J. Hosp Infect. 10, 10–6.

Kabara, J. J. (1980), Nutrition Reviews, 38, 235–7.

Kabara, J. J. (1983) Medium Chain Fatty Acids and Esters, in Antimicrobials in Foods. Edited by A. L. Branen & P. M. Davidson, New York, Marcel Dekker, 109–139.

Kapral, F. A., Smith, S. and Lal, D. (1992), The esterification of fatty acids by *Staphylococcus aureus* fatty acid modifying enzyme (FAME) and its inhibition by glycerides, J. Med. Microbiol, 37, 235–7.

Knudsen, B. B. and Avnstorp, C. (1991), Chlorhexidine gluconate and acetate in patch testing, Contact Dermatitis 24, 45–49.

Ojajarvi, J. (1978), Aspects of infection control, Hands as Vectors of disease, Imperial Chemical Industries Limited, Pharmaceutical Division, Alderley Park Macclesfield, Cheshire, England.

Reynolds, N. J. and Harman, R. R. (1990), Allergic contact dermatitis from chlorhexidine diacetate in a skin swab, Contact Dermatitis 22, 103–4.

What is claimed is:

1. A protective composition for inhibiting bacterial, viral and fungal growth on the skin comprising:
   (i) a physiologically acceptable carrier or base;
   (ii) a preservative;
   (iii) an active ingredient for protecting the skin; and
   (iv) a skin protectant;
   wherein the active ingredient is a combination of a salt of a $C_8$ to $C_{20}$ fatty acid and one or more parabens, having synergistic antimicrobial activity.

2. A protective composition according to claim 1, wherein the salt of a $C_8$ to $C_{20}$ fatty acid is a salt of lauric acid.

3. A protective composition according to claim 1 or 2, wherein the salt of a $C_8$ to $C_{20}$ fatty acid is present in an amount of 0.05% to 5% w/v.

4. A protective composition according to claim 1 or 2, wherein the salt of a $C_8$ to $C_{20}$ fatty acid is present in an amount of 0.2% to 1% w/v.

5. A protective composition according to claim 1, wherein the paraben is methyl paraben, propyl paraben or a combination thereof.

6. A protective composition according to claim 1, wherein the composition comprises methyl and propyl parabens in about a 1:1 ratio (w/v).

7. A protective composition according to claim 6, wherein the methyl and propyl parabens are present in an amount of 0.05% to 1%(w/v).

8. A protective composition according to claim 6, wherein the methyl and propyl parabens are present in an amount of 0.2% to 0.3%(w/v).

9. A protective composition according to claim 1 comprising a salt of lauric acid and 0.2% to 1% (w/v) of at least one paraben.

10. A protective composition according to claim 1, in the form of a hand cream, body lotion, a cream or lotion for topical application to the skin, a liquid soap, soap bar, shampoo or mouth wash.

11. A method for inhibiting the growth of bacteria, fungi, and viruses in a subject, which comprises administering to said subject a synergistic combination of a salt of a $C_8$ to $C_{20}$ fatty acid together with at least one paraben.

12. A method according to claim 11, wherein the bacteria are selected from the group consisting of methicillin resistant *Staphylococcus aureus* (MRSA), vancomycin resistant Enterococci (VRE) and resistant strains of coliforms and pseudomonads.

* * * * *